United States Patent
Friscic et al.

(10) Patent No.: US 10,099,203 B2
(45) Date of Patent: Oct. 16, 2018

(54) METHOD FOR THE PREPARATION OF METAL-ORGANIC COMPOUNDS

(71) Applicant: THE ROYAL INSTITUTION FOR THE ADVANCEMENT OF LEARNING/MCGILL UNIVERSITY, Montreal (CA)

(72) Inventors: Tomislav Friscic, Verdun (CA); Chao-Jun Li, Brossard (CA); Simon Girard, Montreal (CA); Cristina Mottillo, St-Léonard (CA); Christopher Walter Nickels, Montreal (CA)

(73) Assignee: THE ROYAL INSTITUTION FOR THE ADVANCEMENT OF LEARNING/MCGILL UNIVERSITY, Montreal (CA)

(*) Notice: Subject to any disclaimer, the term of this patent is extended or adjusted under 35 U.S.C. 154(b) by 0 days.

(21) Appl. No.: 15/552,530

(22) PCT Filed: Feb. 22, 2016

(86) PCT No.: PCT/CA2016/050172
§ 371 (c)(1),
(2) Date: Aug. 22, 2017

(87) PCT Pub. No.: WO2016/134459
PCT Pub. Date: Sep. 1, 2016

(65) Prior Publication Data
US 2018/0043330 A1    Feb. 15, 2018

Related U.S. Application Data

(60) Provisional application No. 62/119,436, filed on Feb. 23, 2015.

(51) Int. Cl.
| | | |
|---|---|---|
| B01J 20/22 | (2006.01) | |
| B01J 20/30 | (2006.01) | |
| C07C 51/41 | (2006.01) | |
| C30B 29/54 | (2006.01) | |
| C07D 233/58 | (2006.01) | |
| C07F 1/08 | (2006.01) | |
| C07F 3/06 | (2006.01) | |
| C07D 213/79 | (2006.01) | |

(52) U.S. Cl.
CPC ......... B01J 20/226 (2013.01); B01J 20/3085 (2013.01); C07C 51/412 (2013.01); C07D 213/79 (2013.01); C07D 233/58 (2013.01); C07F 1/08 (2013.01); C07F 3/06 (2013.01); C30B 29/54 (2013.01)

(58) Field of Classification Search
None
See application file for complete search history.

(56) References Cited

U.S. PATENT DOCUMENTS

| | | |
|---|---|---|
| 8,466,284 B2 | 6/2013 | Chapman et al. |
| 2014/0179514 A1* | 6/2014 | Matzger ............... B01J 20/3085 502/165 |

FOREIGN PATENT DOCUMENTS

CA    2909372 A1    12/2014

OTHER PUBLICATIONS

Banerjee, R., Furukawa, H., Britt, D., Knobler, C., O'Keeffe, M., Yaghi, O.M., "Control of Pore Size and Functionality in Isoreticular Zeolitic Imidazolate Frameworks and their Carbon Dioxide Selective Capture Properties", J. Am. Chem. Soc. 2009, 131, 3875-3877.s.
Batten, S.R., Champness, N.R., Chen, X.-M., Garcia-Martinez, J., Kitagawa, S., Ohrstrom, L., O'Keeffe, M., Suh, M. P., Reedijk, J., "Coordination polymers, metal-organic frameworks and the need for terminology guidelines" CrystEngComm 2012, 14, 3001-3004.
Bayliss, P.A., Ibarra, I.A., Perez, E., Yang, S., Tang, C.C., Poliakoff, M., Schroder, M., "Synthesis of metal-organic frameworks by continuous flow" Green Chem. 2014, 16, 3796-3802.
Beldon, P.J., Fabian, L., Stein, R.S., Thirumurugan, A., Cheetham, A.K., Friscic, T., "Rapid Room-Temperature Synthesis of Zeolitic Imidazolate Frameworks by Using Mechanochemistry", Angew. Chem. Int. Ed. 2010, 49, 9640-9643.
Czaja, A.U., Trukhan, N., Muller, U., "Industrial applications of metal-organic frameworks" Chem. Soc. Rev. 2009, 38, 1284-1293.
Farha, O.K., Eryazici, I., Jeong, N.C., Hauser, B.G., Wilmer, C.E., Sarjeant, A.A., Snurr, R.Q., Nguyen, S.T., Yazaydin, A.O., Hupp, J.T., "Metal-Organic Framework Materials with Ultrahigh Surface Areas: Is the Sky the Limit?" J. Am. Chem. Soc. 2012, 134, 15016-15021.
Farha, O.K., Joseph T. Hupp, J.T., "Rational Design, Synthesis, Purification, and Activation of Metal-Organic Framework Materials". Accounts of Chemical Research, 2010, 43, 1166-1175.
Ibarra, I.A., Bayliss, P.A., Perez, E., Yang, S., Blake,Aa.J., Nowell, H., Allan, D.R., Poliakoff, M., Schroder, M., "Near-critical water, a cleaner solvent for the synthesis of a metal-organic framework" Green Chem. 2012, 14, 117-122.
Mondloch, J.E., Karagiaridi, O., Farha, O.K, Hupp, J.T., "Activation of Metal-Organic Framework Materials". CrystEngComm, 2013, 15, 9258-9264.
Mottillo, C., Lu, Y., Pham, M.-H., Cliffe, M.J., Do, T.-O., Friscic, T., "Mineral neogenesis as an inspiration for mild, solvent-free synthesis of bulk microporous metal-organic frameworks from metal (Zn, Co) oxides" Green. Chem. 2013, 15, 2121-2131.

(Continued)

*Primary Examiner* — Clinton A Brooks
(74) *Attorney, Agent, or Firm* — Goudreau Gage Dubuc; Isabelle Pelletier (57) ABSTRACT

A method for the preparation of a metal-organic compound is provided. This method comprises the steps of (a) providing at least one metal precursor, (b) providing at least one bridging organic ligand, and (c) exposing together the metal precursor and the ligand to liquid $CO_2$ or supercritical $CO_2$ as a reaction medium, thereby producing said metal-organic compound.

20 Claims, 11 Drawing Sheets

(56) References Cited

OTHER PUBLICATIONS

Nelson, A.P., Farha, O.K., Mulfort, K.L., Hupp, J.T., "Supercritical Processing as a Route to High Internal-Surface Areas and Permanent Microporosity in Metal-Organic Framework Materials", J. Am. Chem. Soc. 2009, 131, 458-460.

Park, K.S., Ni, Z., Cote, A.P., Choi, J.Y., Huang, R., Uribe-Romo, F.J., Chae, H.K., O'Keeffe, M., Yaghi, O.M. "Exceptional chemical and thermal stability of zeolitic imidazolate frameworks" Proc. Natl. Acad. Sci., 2006, 103, 10186-10191.

Pichon, A., Lazuen-Garay, A., James, S.L., "Solvent-free synthesis of a microporous metal-organic framework" CrystEngComm, 2006, 8, 211-214.

Stock, N., Biswas, S., "Synthesis of Metal-Organic Frameworks (MOFs): Route to Various MOF Topologies, Mlorphologies, and Composites". Chemical Reviews, 2011, 112, 933-969.

Zhang, J.-P., Zhang, Y.-B., Lin, J.-B., Chen, X.-M., "Metal Azolate Frameworks: From Crystal Engineering to Functional Materials" Chem. Rev. 2012, 112, 1001-1033.

International Search Report and Written Opinion, dated May 4, 2016.

\* cited by examiner

Pressure-Temperature phase diagram for $CO_2$.

METHOD FOR THE PREPARATION OF METAL-ORGANIC COMPOUNDS

CROSS REFERENCE TO RELATED APPLICATIONS

This application a National Entry Application of PCT application no PCT/CA2016/050172 filed on Feb. 22, 2016 and published in English under PCT Article 21(2), which itself claims benefit of U.S. provisional application Ser. No. 62/119,436, filed on Feb. 23, 2015. All documents above are incorporated herein.

FIELD OF THE INVENTION

The present invention relates to methods for the preparation of metal-organic compounds. More specifically, the present invention is concerned with the use of $CO_2$ as the reaction medium in the preparation of metal-organic compounds, in particular metal-organic frameworks.

BACKGROUND OF THE INVENTION

Metal-Organic Frameworks (MOFs) are compounds consisting of metal ions or clusters coordinated to (often rigid) organic molecules to form one-, two-, or three-dimensional structures. These structures can be porous or non-porous.

MOFs are composed of two major components: a metal ion or cluster of metal ions and an organic molecule. The organic units are typically mono-, di-, tri-, or tetravalent ligands. The choice of metal and linker dictates the structure and hence properties of the MOF. For example, the metal's coordination preference influences the size and shape of pores by dictating how many ligands can bind to the metal and in which orientation.

MOFs can be considered metal-organic analogues of zeolites, sometimes exhibiting framework topologies found in zeolites. Zeolites are widely used materials that have a hydrous framework of aluminosilicates or their derivatives and have relatively large channels. They are used as molecular sieves, desiccants, adsorbent, ion exchangers, and catalysts. However, many existing zeolites are not easy to manipulate at the molecular level, such that there has been an increasing trend towards other microporous materials based on building blocks other than silicon, aluminium and oxygen, specifically metal-organic materials involving metal species and organic groups.

Zeolitic imidazolate frameworks (ZIFs) are a class of metal-organic frameworks that are topologically similar or identical to zeolites. ZIFs are composed of tetrahedrally-coordinated transition metal ions (e.g. Fe, Co, Cu, Zn) connected by organic imidazole linkers.

The introduction of porous metal-organic frameworks into the area of commercially-synthesized and distributed materials has generated the need to develop clean and efficient methodologies for the synthesis of such materials. Whereas the space of porous metal-organic materials now spans thousands of compounds, the associated synthetic procedures are often solvothermal and low-yielding or demand the use of often thermally- or hydrolytically-sensitive organic solvents. Despite such hindrances, which are particularly augmented when considering industrial manufacture, solvothermal synthesis of porous materials remains a method of choice due to the potential of providing single crystal samples suitable for structural characterization.

However, for materials of known or expected commercial application structural characterization is of secondary importance and the development of more efficient and environmentally-friendly synthetic methods is justified. In that context, sonochemical synthesis has opened new opportunities in reducing the synthesis time and energy costs associated with the synthesis of metal-organic porous materials.

Similarly, solvent-reduced or solvent-free methods such as mechanosynthesis or accelerated aging have enabled the synthesis of pillared MOFs or zeolitic imidazolate frameworks (ZIFs) directly from basic metal oxide precursors, such as ZnO, CuO and CoO.

Finally, the application of simple salt catalysts has enabled the transformation of metal oxides into porous MOFs, metallodrugs or pharmaceutical derivatives either by mechanochemical ion- and liquid-assisted grinding (ILAG) or by a low-energy accelerated aging process. In that context, particular attention has been given to the synthesis of ZIFs, due to their chemical simplicity as well as their attractive carbon dioxide storage properties.

SUMMARY OF THE INVENTION

In accordance with the present invention, there is provided:

1. A method for the manufacture of a metal-organic compound, the method comprising the steps of:
   (a) providing at least one metal precursor,
   (b) providing at least one bridging organic ligand, and
   (c) exposing together the metal precursor and the ligand to liquid $CO_2$ or supercritical $CO_2$ as a reaction medium, thereby producing said metal-organic compound.
2. The method of item 1, wherein during step (c), the metal precursor and the ligand are stirred with the liquid $CO_2$ or supercritical $CO_2$.
3. The method of item 1 or 2, wherein during step (c), the metal precursor and the ligand are together exposed to supercritical $CO_2$.
4. The method of item 1 or 2, wherein during step (c), the metal precursor and the ligand are together exposed to liquid $CO_2$.
5. The method of any one of items 1 to 4, wherein step c) is carried out at a temperature ranging between about 0° C. and about 100° C.
6. The method of item 5, wherein step c) is carried out at a temperature ranging between about 20° C. and about 90° C.
7. The method of item 6, wherein step c) is carried out at a temperature ranging between about 40° C. and about 80° C.
8. The method of item 7, wherein step c) is carried out at a temperature ranging between about 50° C. and about 70° C.
9. The method of item 8, wherein step c) is carried out at a temperature of about 60° C.
10. The method of any one of items 1 to 9, wherein step c) is carried out at a pressure ranging between about 80 bar and about 140 bar.
11. The method of item 10, wherein step c) is carried out at a pressure ranging between about 90 bar and about 140 bar.
12. The method of item 11, wherein step c) is carried out at a pressure ranging between about 100 bar and about 140 bar.
13. The method of item 12, wherein step c) is carried out at a pressure ranging between about 110 bar and about 140 bar.

14. The method of item 13, wherein step c) is carried out at a pressure ranging between about 120 bar and about 140 bar.
15. The method of item 14, wherein step c) is carried out at a pressure of about 130 bar.
16. The method of any one of items 1 to 15, further comprising the step of (d) isolating the produced metal-organic compound from the liquid $CO_2$ or supercritical $CO_2$ by evaporating the liquid $CO_2$ or supercritical $CO_2$.
17. The method of any one of items 1 to 16, further comprising the step of (e) isolating the metal-organic compound from unreacted metal precursor and/or unreacted bridging organic ligand.
18. The method of any one of items 1 to 17, wherein the metal precursor contains a metal that is:
from groups 1 to 12 of the Periodic Table, or
Ga, Ge, In, Sn, Sb, Tl, Pb, or Bi, or
a lanthanide.
19. The method of any one of items 1 to 18, wherein the metal precursor contains a metal in ionic form.
20. The method of any one of items 1 to 19, wherein the metal precursor contains a metal in the form of an oxide or a salt.
21. The method of any one of items 1 to 20, wherein the metal-organic compound is a metal-organic framework.
22. The method of any one of items 1 to 21, wherein the metal-organic compound is a zeolitic imidazolate framework.
23. The method of any one of items 1 to 22, wherein the metal precursor contains Zn.
24. The method of any one of items 1 to 23, wherein the metal precursor is ZnO.
25. The method of any one of items 1 to 24, wherein the ligand is a substituted or unsubstituted imidazole.
26. The method of any one of items 1 to 25, wherein the ligand is 2-methylimidazole.
27. The method of any one of items 1 to 26, wherein the metal-organic compound is ZIF-8.
28. The method of any one of items 1 to 21, wherein the metal-organic compound is a carboxylate-based metal-organic framework.
29. The method of any one of items 1 to 21 and 28, wherein the metal precursor contains Cu.
30. The method of any one of items 1 to 21, 28, and 29, wherein the metal precursor contains Cu(II).
31. The method of any one of items 1 to 21 and 28 to 30, wherein the metal precursor is copper(II) acetate.
32. The method of any one of items 1 to 21 and 28 to 31, wherein the ligand is a carboxylic acid or diacid.
33. The method of any one of items 1 to 21 and 28 to 32, wherein the ligand is isonicotinic acid.
34. The method of any one of items 1 to 21 and 28 to 33, wherein the ligand is trimesic acid.
35. The method of any one of items 1 to 21 and 28 to 34, wherein the metal-organic compound is copper(II) isonicotinate metal-organic framework or copper(II) trimesate metal-organic framework.
36. The method of item 35, wherein the metal-organic compound is copper(II) isonicotinate metal-organic framework.
37. The method of item 35, wherein the metal-organic compound is copper(II) trimesate metal-organic framework.

BRIEF DESCRIPTION OF THE DRAWINGS

In the appended drawings:
FIG. 12 shows the X-ray powder diffraction pattern of the product of Example 4 (top) with that of the copper(II)

acetate monohydrate reactant (middle) and the pattern simulated for one of the reported crystal structures of the copper (II) isonicotinate framework (bottom, shown is the pattern simulated for the structure under the CSD code BAH-GUN04)

DETAILED DESCRIPTION OF THE INVENTION

Turning now to the invention in more detail, there is provided a method for the manufacture of a metal-organic compound, the method comprising the steps of:
providing at least one metal precursor,
providing at least one bridging organic ligand, and
exposing the metal precursor together with the ligand to liquid $CO_2$ or supercritical $CO_2$ as a reaction medium, thereby producing said metal-organic compound.

The present invention is based on the unexpected finding by the present inventors that liquid $CO_2$ and supercritical $CO_2$ can act as media for the synthesis of (i.e. as a reaction medium for) metal-organic compounds (in particular MOFs) directly from various metal precursors. In particular, some of these metal precursors—mostly inorganic, often oxides—may not be amenable to such synthesis by other methods. To the best of the inventors' knowledge, this is the first consideration of liquid $CO_2$ and/or supercritical $CO_2$ as synthetic media for preparing MOFs, as well as the first application of liquid $CO_2$ and/or supercritical $CO_2$ for conducting reactions on transition metal oxides. The method described herein may open up an entirely new, never previously explored approach for the clean synthesis of metal-organic compounds, in particular MOFs.

Therefore, it is to be understood that the method of the invention is usually carried in the absence of other solvents, i.e. solvents other than liquid $CO_2$ and/or supercritical $CO_2$. In the method of the invention, the reaction between the metal precursor and bridging organic ligand occurs when these are exposed together to liquid $CO_2$ or supercritical $CO_2$. In other words, the liquid $CO_2$ or supercritical $CO_2$ is the reaction medium. The metal-organic compound is thus preferably produced in the absence of other solvents or if other such solvents are present, they are present in minor amounts and/or they do not serve as reaction medium.

The nature of the metal-organic compound that can be produced by the method of the invention is not particularly limited. The produced metal-organic compound can be, for example:
a non-porous coordination polymer (i.e. a compound consisting of a single metal ion, or a more complex metal-based subunit (cluster), and an organic ligand, with 1-dimensional, 2-dimensional or 3-dimensional topology based on metal-ligand bonds);
a discrete metal complex (molecular or ionic units that are held by metal-ligand bonds);
a metallodrug, for example:
bismuth salicylate and subsalicylate, which are the active components of Pepto-Bismol® and also examples of coordination polymers;
cis-platin and other transition metal compounds used for cancer treatment, and
carbon monoxide releasing molecules (CORMs), which are often discrete complexes, or
a metal-organic framework (MOF).

In preferred embodiments, the produced metal-organic compound is a metal-organic framework (MOFs). The nature of the metal-organic frameworks that can be produced by the method of the invention is not particularly limited. These can be, for example, 2D or 3D MOFs. These may be porous or non-porous. More preferably, microporous metal-organic frameworks are produced.

Non-limiting examples of preferred porous or non-porous metal-organic frameworks include:
zeolitic imidazolate frameworks (ZIFs),
metal azolate frameworks (i.e. metal-organic frameworks made of metal ions and azolate anions),
pillared metal-organic frameworks (i.e. metal-organic frameworks in which sheets or chains of metal carboxylate are bridged into galleries by additional ligands, called pillaring ligands),
Materiels de l'Institut Lavoisier (MILs) (i.e. metal-organic frameworks consisting of oxo- and/or hydroxo and/or fluorido clusters of trivalent metal ions bridged by extended carboxylic acid ligands),
carboxylate-based frameworks in general (including, but not limited to e.g. the trimesate-, isonicotinate-, fumarate, oxalate, acetylenedicarboxylate, terephthalate, 2,5-dihydroxyterephthalate, and benzene-1,3,5-tris(benzenecarboxylate)-based frameworks as well as the UiO-66 and UiO-67 families of metal-organic frameworks), and
coordination polymers consisting of metal halides and neutral ligands, for example, but not limited to ligands of pyridine, imidazole or nitrile type.

Of note, multi-metal MOFs (and metal-organic compounds generally) can be produced simply by using two or more metals. Multi-bridging-ligand MOFs (and metal-organic compounds generally) can be produced simply by using two or more bridging organic ligands. Further, multi-metal and multi-bridging-ligand MOFs (and metal-organic compounds generally) can be similarly produced.

It is also possible to form interpenetrated structures, i.e. structures which consist of more than one network and are structurally interlocked, but which are not chemically bonded to each other. The abovementioned pillared layer structures may include examples of this.

It is also possible to form framework materials based on SBUs (secondary building units), 'inclusion' or 'host-guest' materials as well as framework materials whose structures are directed by additional templating agents.

More preferred MOFs are zeolitic imidazolate frameworks (ZIFs), such as ZIF-8, and carboxylate-based frameworks, such as copper(II) trimesate and copper(II) isonicotinate. Of note, ZIF-1 to -12 have been described by Park et al. in the Proc. Natl. Acad. Sci. USA 2006 103 (27) 10186-10191. In particular, sodalite-topology and zeolite RHO-topology zeolitic imidazolate frameworks (ZIFs) are preferred.

There is no obvious limitation on the selection of starting materials. The starting materials will simply be chosen to provide the desired metal-organic compound as well-known to the skilled person.

The metal precursor, which is typically a metal in an ionic form, may contain any metal from groups 1-12 of the Periodic Table, and also Ga, Ge, In, Sn, Sb, Tl, Pb, Bi, as well as lanthanide elements. Preferred metals are Zn and Cu (particularly Cu(II)).

The ionic form of the metal may be an oxide form or a salt form (such as carbonates, hydroxides, nitrates, chlorides, sulfates, acetates, and the like). Compared to organic solvent based methods, it is an advantage of the method of the invention that it does not require the use of metal precursors that are soluble in organic solvents (such as nitrates and chlorides, which are often toxic, corrosive, and/or explosive). A preferred ionic form is the oxide form, which can often be extracted directly from minerals and is thus generally inexpensive. Of note, metal oxides are typically not soluble in organic solvents.

A preferred metal in ionic form is Zn in oxide form, i.e. ZnO. Another preferred metal in ionic form is Cu(II) in acetate form, i.e. copper(II) acetate, for example as a monohydrate.

The bridging organic ligand can be any one of a large number of known organic ligands. However, organic ligands which comprise a bridging atom having at least one non-binding doublet (i.e. a free pair of electrons) available, like oxygen, nitrogen, phosphorus or sulphur, are preferred. Suitable ligands include azoles, imidazoles, carboxylates, pyridines, amines, and carboxylic acids and/or diacids. Preferred ligands are substituted or unsubstituted imidazoles. Preferred substituted imidazoles include 2-methylimidazole, 2-H-imidazole, imidazole-2-carbaldehyde, benzimidazole, and 2-ethylimidazole. Other preferred ligands include carboxylic acids and diacids, such as isonicotinic acid.

The table below provide non-limiting examples of reactants that can be used together to produce metal-organic compounds.

| Metal | Bridging organic ligand | Metal-organic compound |
|---|---|---|
| zinc | 2-methylimidazole | ZIF-8 |
| zinc | imidazol-2-carboxaldehyde | ZIF-90 |
| copper | isonicotinic acid | copper(II) isonicotinate |
| copper | trimesic acid | HKUST-1 |
| cobalt | 2-methylimidazole | ZIF-67 |
| zinc | terephthalic acid and 1,4-diazabicyclo[2.2.2]octane (dabco) | pillared MOF |
| zinc | terephthalic acid and 4,4'-dipyridyl | pillared MOF |
| aluminium | terephtalic acid | MIL-53(Al) |
| iron | terephthalic acid | MIL-53(Fe) |
| magnesium | formic acid | magnesium formate |
| zinc | 2,5-dihydroxyterephthalic acid | Zn-MOF-74 |
| magnesium | 2,5-dihydroxyterephthalic acid | Mg-MOF-74 |
| iron | trimesic acid | MIL-100(Fe) |

Both the metal precursor and the bridging organic ligand will typically be in solid form, preferably in powder form.

In the method of the invention, the metal precursor and the bridging organic ligand are together (i.e. both at the same time in the same vessel) exposed to liquid $CO_2$ or supercritical $CO_2$, preferably supercritical $CO_2$.

The metal precursor and the bridging organic ligand may be mixed together or not prior to exposure to the $CO_2$. Of note, contrary to prior art methods, there is generally no need for the metal precursor and the bridging organic ligand to be ground into an intimate mixture for the reaction to occur.

Figure 1:
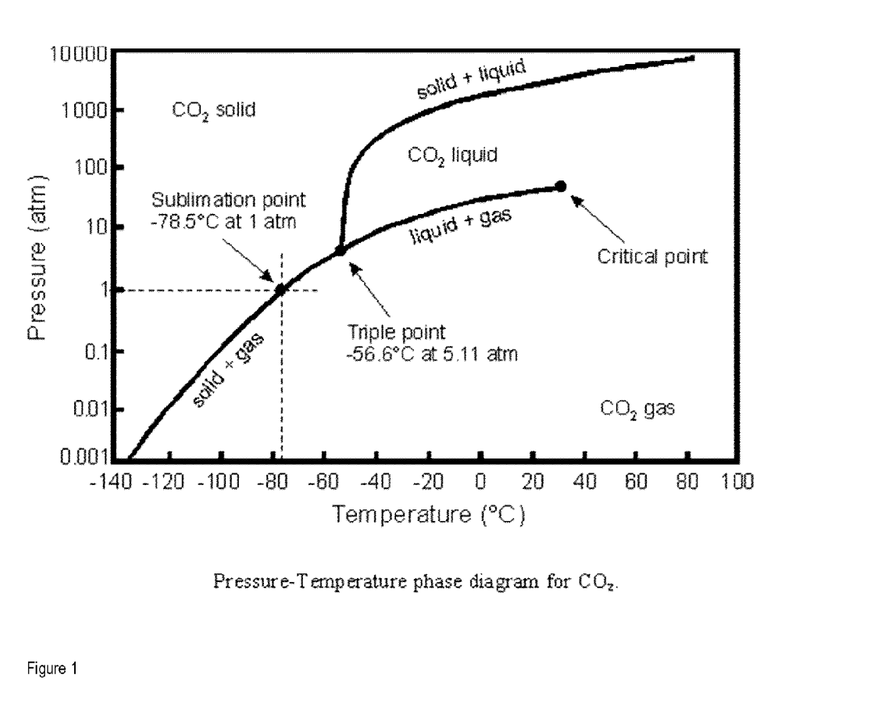
FIG. 1 shows the phase diagram of $CO_2$.

Exposure to liquid $CO_2$ or supercritical $CO_2$ can take place in a reactor maintaining appropriate temperature and pressure to obtain either liquid $CO_2$ or supercritical $CO_2$. The ranges of temperature and pressure in which liquid $CO_2$ or supercritical $CO_2$ are obtained are shown in the phase diagram for $CO_2$ provided as FIG. 1. Any temperature/pressure combination in those ranges can be used in the present method.

Typically, temperatures at the higher end of the range shown in this figure can be used to accelerate the reaction as needed. However, care must be taken that such higher temperature does not cause damage to the desired product or lead to the production of undesired by-products.

With regard to pressure, two contrary effects are at play. First, increased pressure may facilitate the reaction because it brings the reactants closer together. On the other hand, the formation of open metal-organic structures is expected by accompanied with an increase in volume and, therefore to be hindered by higher pressures.

In embodiments, for example the production of zeolitic imidazolate frameworks (ZIFs), and in particular ZIF-8, the temperature during exposure to liquid $CO_2$ or supercritical $CO_2$, preferably supercritical $CO_2$, ranges between about 0° C. and about 100° C., in particular between about 20° C. and about 90° C., preferably between about 40° C. and about 80° C., more preferably between about 50° C. and about 70° C., and most preferably is about 60° C. and/or the pressure during exposure to liquid $CO_2$ or supercritical $CO_2$, preferably supercritical $CO_2$, ranges between about 80 bar and about 140 bar, in particular between about 90 bar and about 140 bar, more particularly between about 100 bar and about 140 bar, preferably between about 110 bar and about 140 bar, more preferably between about 120 bar and about 140 bar, and most preferably is about 130 bar. The Examples below show that these most preferred values of temperature and pressure yield a desired product, such as ZIF-8, in a few minutes rather than several hours.

The metal precursor and the bridging organic ligand together with the liquid $CO_2$ or supercritical $CO_2$ may be stirred or not. Preferably, they are stirred as this generally tends to increase the reaction rate and/or yield.

The method generally does not require any catalyst or additive to be present with the metal precursor, the bridging organic ligand and the liquid $CO_2$ or supercritical $CO_2$. Therefore, in embodiments, the exposition step of the method is carried out in the absence of catalyst and/or additive.

In embodiments, a templating agent may be present. Such agents and their use are well-known to the person skilled in the art of making metal-organic compounds.

In embodiments, the method further comprises the step of isolating the produced metal-organic compound from the liquid $CO_2$ or supercritical $CO_2$ by evaporating the liquid $CO_2$ or supercritical $CO_2$. This can be achieved by bringing the produced metal-organic compound to room temperature and normal pressure (or any other temperature/pressure conditions that will cause the $CO_2$ to evaporate). As the $CO_2$ evaporates, it will leave behind the desired metal-organic compound.

Typically, when stoichiometric ratios of the reactants are used and the reaction is complete, there is generally no unreacted metal precursor and/or unreacted bridging organic ligand left with the metal-organic compound and thus no need to purify the metal-organic compound. However, in alternative embodiments, the method of the invention further comprises the step of isolating the metal-organic compound from unreacted metal precursor and/or unreacted bridging organic ligand. This can be done for example by washing the sample with supercritical carbon dioxide, washing with a common organic solvent (e.g. methanol, ethanol, chloroform, acetone, etc.) or by heating the sample, leading to removal of excess ligand through the gas phase.

Advantages of the Invention

In embodiments, the method of the invention may have one or more of the following advantages.

The method does not require organic solvents.

As such, the method produces materials without included solvents. Indeed, the carbon dioxide that may remain in the pores of the product will evaporate as soon as normal conditions (room temperature and normal pressure) are achieved. This circumvents one of the most important problems of conventional metal-organic framework synthesis. Conventionally, solvents are indeed removed from MOFs by heating under vacuum. This is cumbersome. Also, this approach cannot be applied to MOFs that are heat-sensitive.

Also, the method may generally be considered environmentally-friendly because it does not require organic solvent and also because it has low demands in terms of energy and temperature. The method is also economical as it has increased efficiency in terms of materials, time, cost or energy, compared to the "solvothermal" method of producing MOFs.

The method is furthermore quite simple; requiring a single reaction step. No additive/catalyst is generally required. Furthermore, the MOFs (in particular ZIFs) can generally be obtained directly from inorganic precursors, i.e. simple and often cheap materials such as metal oxides.

Multiple ligands and multiple metal precursors can be used to produce multi-metal and/or multi-bridging-ligand MOFs.

The method can provide known and popular materials. In particular, the method of invention allows the synthesis of the porous sodalite-topology and zeolite RHO-topology zeolitic imidazolate frameworks (ZIFs) by simple reaction of a high-melting and insoluble metal oxide (ZnO) with the organic ligand in the supercritical carbon dioxide medium.

The method appears readily scalable.

The method can provide quantitative yields of the desired metal-organic compound, generally without using large excesses of either the metal-containing precursor or the ligand.

Definitions

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% or plus or minus 5% of the numerical value qualified.

Unless otherwise defined, all technical and scientific terms used herein have the same meaning as commonly understood by one of ordinary skill in the art to which this invention belongs.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

The present invention is illustrated in further details by the following non-limiting examples.

Figure 2:
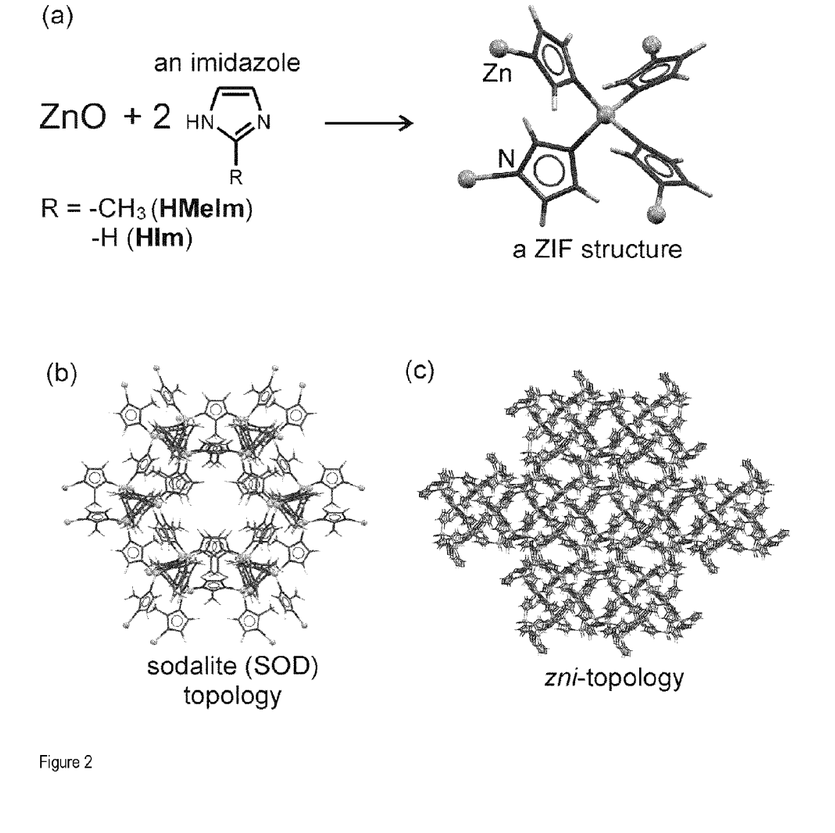
FIG. 2 shows (a) the transformation of zinc oxide into zeolitic imidazolate frameworks (ZIFs); (b) a fragment of a porous SOD-topology structure found in ZIF-8, and (c) a fragment of the non-porous zni-topology structure, found in zni-$Zn(Im)_2$.

Example 1—Synthesis of ZIF-8 in Supercritical $CO_2$ $scCO_2$ (supercritical $CO_2$) was used as the medium for the synthesis of ZIF-8 starting from a 1:2 stoichiometric mixture of ZnO and 2-methylimidazole (HMeIm, FIG. 2a) along with 5 mol % (with respect to ZnO) of ammonium sulphate $(NH_4)_2SO_4$. Following 10 hours or 18 hours exposure to $scCO_2$ at 90 bar pressure and 45° C., powder X-ray diffraction (PXRD) analysis of the reaction mixture revealed the formation of ZIF-8. Specifically, the PXRD pattern clearly demonstrated characteristic reflections of ZIF-8 at 2theta diffraction angles 7.40, 10.4° and 12.8°, along with stronger reflections of HMeIm and ZnO reactants. After a longer reaction time of 48 hours, the reaction mixture consisted of almost pure ZIF-8, as evidenced by only very weak reflections of ZnO reactant.

Figure 3:
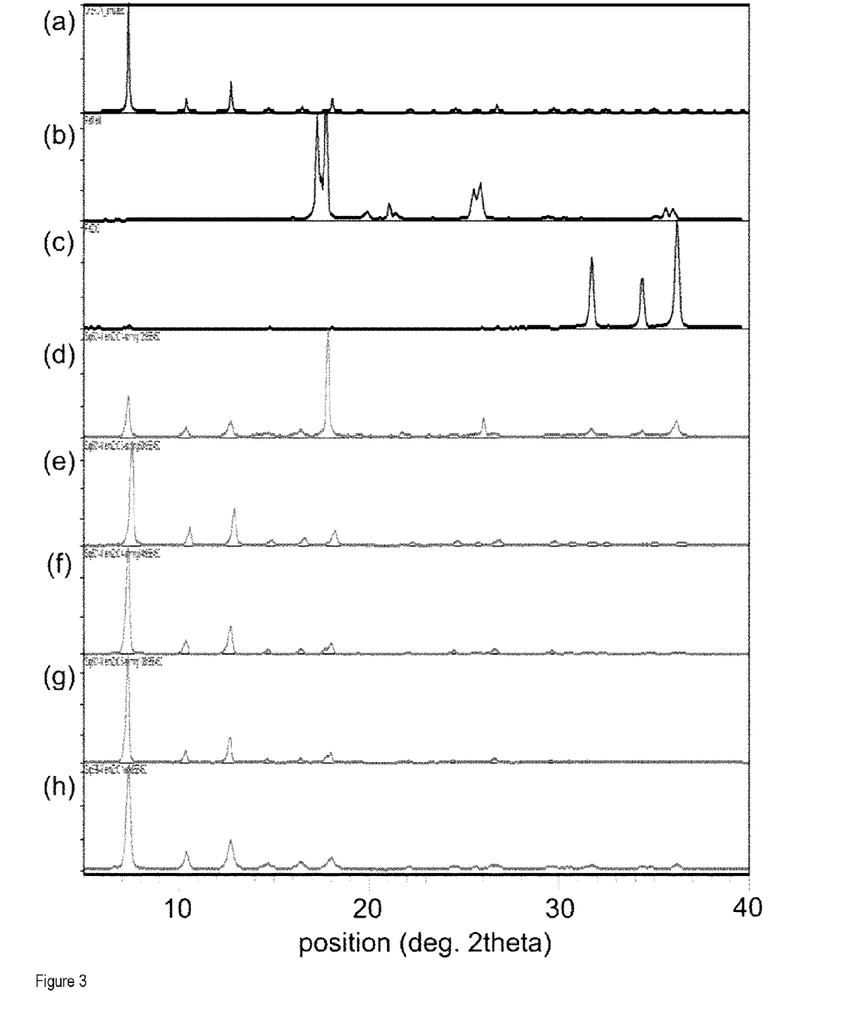
FIG. 3 shows PXRD patterns for the synthesis of the metal-organic framework ZIF-8 in supercritical $CO_2$ (95 bar, 45° C.): (a) simulated for the crystal structure of ZIF-8 (CSD code OFERUN); (b) HMeIm reagent; (c) reagent ZnO; (d) reaction mixture after 12 hours; (e) reaction mixture after 60 hours; (f) reaction mixture after 84 hours; (g) reaction mixture after 108 hours; and (h) reaction mixture after 168 hours (1 week)

As the next step, the extent of reaction in the absence of the $(NH_4)_2SO_4$ additive was evaluated. In contrast to mechanochemical and accelerated aging reactions, the formation of ZIF-8 proceeded readily even without ammonium sulphate (see FIG. 3). The PXRD pattern of the reaction mixture following 60 hours exposure exhibited only weak reflections of ZnO, and after 84 hours these reflections were almost undetectable. Consequently, the $scCO_2$ medium allows the spontaneous, additive-free conversion of ZnO into ZIF-8, representing an alternative to extended mechanochemical procedures or reactions in molten HMeIm. The comparison of PXRD patterns clearly indicated the formation of ZIF-8 as the only product of the reaction mediated by $scCO_2$.

Figure 4:
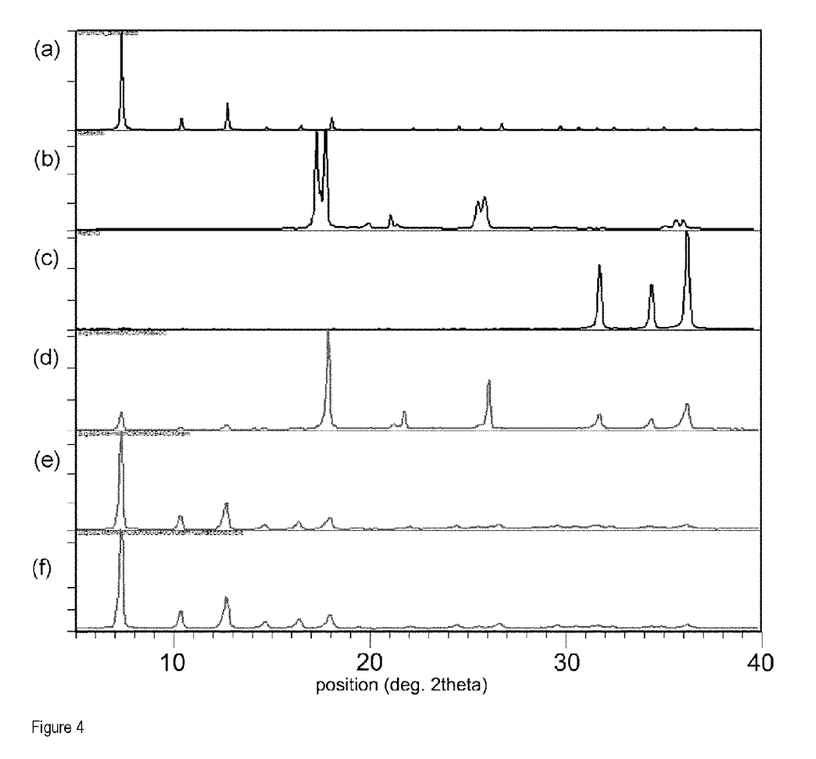
FIG. 4 shows PXRD patterns for the synthesis of the metal-organic framework ZIF-8 in supercritical $CO_2$ at one gram scale (90 bar, 40° C.): (a) simulated for the crystal structure of ZIF-8 (CSD code OFERUN); (b) HMeIm reagent; (c) reagent ZnO; (d) reaction mixture after 20 hours; (e) reaction mixture after 90 hours; and (f) reaction mixture after 118 hours.

Importantly, the reaction could also be readily scaled to one gram scale without loss in conversion (see FIG. 4). Again, the comparison of PXRD patterns clearly shows gram-scale formation of ZIF-8, mediated by $scCO_2$.

Figure 5:
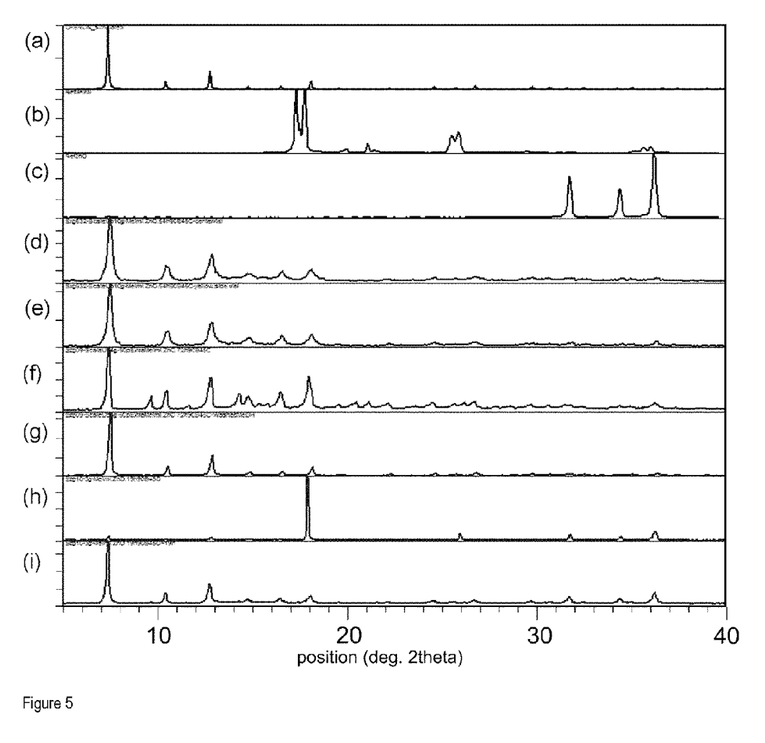
FIG. 5 shows PXRD patterns for the synthesis of the metal-organic framework ZIF-8 in supercritical $CO_2$ at >1 gram scale (90 bar, 45° C.): (a) simulated for the crystal structure of ZIF-8 (CSD code OFERUN); (b) HMeIm reagent; (c) reagent ZnO; (d) and (e) 10 gram reaction mixture after 54 hours exposure to sc$CO_2$; (f) reaction at 4 gram scale, using 50 mol % excess HMeIm after 72 hours exposure to sc$CO_2$; (g) sample (f) after washing with methanol, demonstrating the absence of ZnO reactant; (h) three gram reaction mixture after 19 hours; and (i) 38 hours exposure to sc$CO_2$.

Attempts to perform the conversion at 10 gram scale were also successful, leading to almost complete disappearance of the ZnO reactant within 54 hours (see FIG. 5).

The spontaneous conversion of ZnO and HMeIm into ZIF-8 in scCO$_2$ is in contrast to reactivity conventionally observed for this system. In order to better understand the underlying reactivity, we explored the scCO$_2$-mediated synthesis of ZIFs using different reagents. We first speculated that the formation of ZIF-8 could be mediated by the formation of a carbonate phase. However, exposure of zinc oxide to scCO$_2$ over prolonged periods of time showed no evidence of any new crystalline phases besides ZnO. Moreover, attempts to conduct ZIF-8 synthesis directly from commercially available basic zinc carbonate also failed. This unexpected difference in reactivity of ZnO and basic zinc carbonate in ZIF synthesis is in contrast to previous experiences using mechanochemical reactivity, where carbonates were often more reactive than corresponding oxides.

Figure 6:
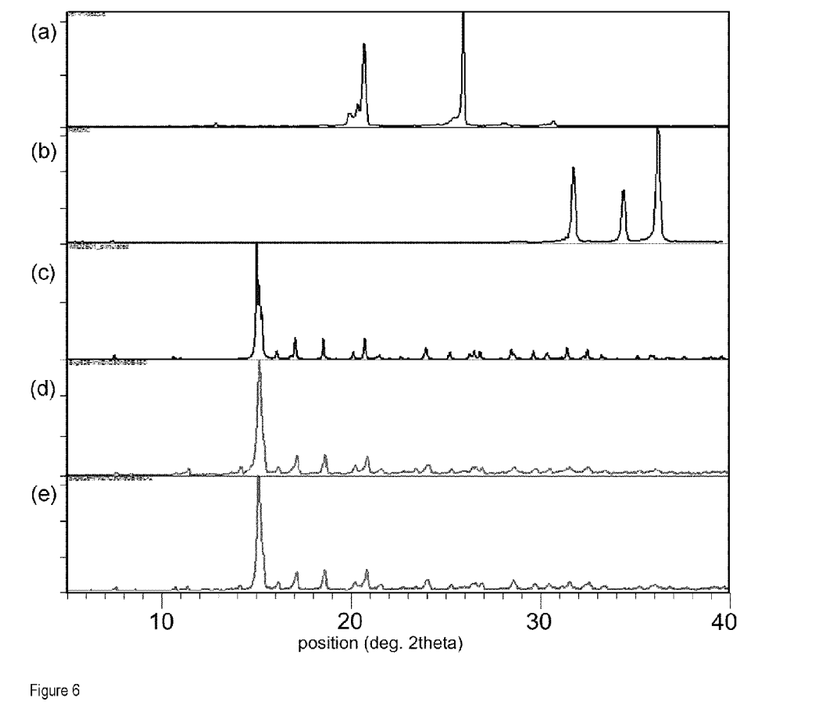
FIG. 6 shows PXRD patterns for the synthesis of the metal-organic framework zni-$Zn(Im)_2$ in supercritical $CO_2$ at 90 bar and 45° C.: (a) HIm reagent; (b) reagent ZnO; (c) simulated for zni-$Zn(Im)_2$ (CSD code IMIDZB01); and (d) and (e) samples of two repeated experiments after 30 hours.

Finally, we explored the reactivity of unsubstituted imidazole (Him) against zinc oxide (see FIG. 6). After 30 hours exposure to supercritical carbon dioxide at a pressure of 90 bar and a temperature of 45° C., the stoichiometric 1:2 ratio of ZnO and HIm fully transformed to the non-porous framework with zni-topology, zni-Zn(Im)$_2$ (see FIG. 2c).

Figure 7:
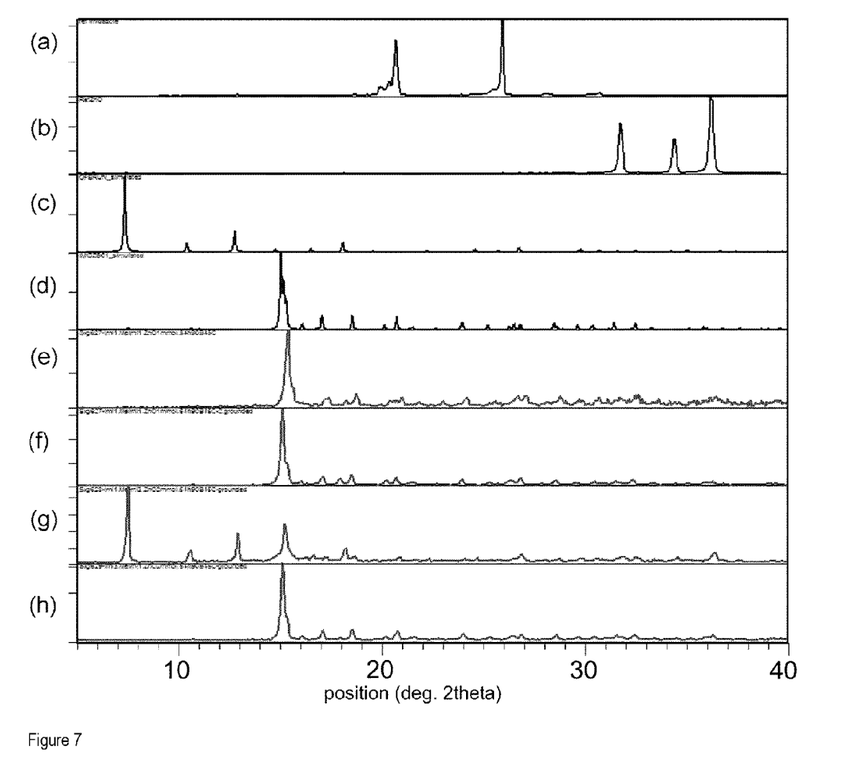
FIG. 7 shows PXRD patterns for the synthesis of metal-organic frameworks from ZnO and mixtures of HIm and HMeim in supercritical $CO_2$ at 90 bar and 45° C.: (a) HIm reagent; (b) reagent ZnO; (c) simulated for SOD-topology $Zn(MeIm)_2$ (CSD code OFERUN); (d) simulated for zni-topology $Zn(Im)_2$ (CSD code IMIDZB01); (e) and (f) two samples of reactions conducted for 54 hours using a 1:1 ratio of HIm and HMeim; (g) sample of the reaction conducted for 54 hours using a 1:3 stoichiometric ratio of HIm and HMeIm; and (h) sample of the reaction involving a 3:1 ratio of HIm and HMeIm after 54 hours in the sc$CO_2$ environment.

The established reactivity of ZnO with HIm, as well as HMeIm under supercritical CO$_2$ suggests the opportunity to also synthesize ZIF materials based on mixtures of ligands. The possibility to synthesize mixed-ligand frameworks in scCO$_2$ was explored by exposing a reaction mixture containing one equivalent of ZnO and two equivalents of a 1:1 stoichiometric mixture of HMeIm and HIm to a supercritical carbon dioxide environment at 90 bar and 45° C. (see FIG. 7). After 54 hours exposure, PXRD analysis revealed the formation of a material isostructural with zni-topology Zn(Im)$_2$ and disappearance of X-ray reflections of the reactant imidazoles and ZnO. Repeating the same experiment, but with a 3:1 respective stoichiometric mixture of HIm and HMeIm yielded the same result. However, if the respective stoichiometric ratio of HIm and HMeIm was 1:3 the PXRD pattern was consistent with a mixture of ZIFs with zni- and SOD-topology (see FIG. 2b). Consequently, these experiments reveal that the reaction of ZnO with a mixture of HIm and HMeim leads to a zni-topology material as long as the ratio of HIm:HMeIm is equal or greater than 1. If HMeIm is the dominant component in the mixture of the two imidazoles, the system produces a mixture of SOD- and zni-topology materials.

Figure 8:
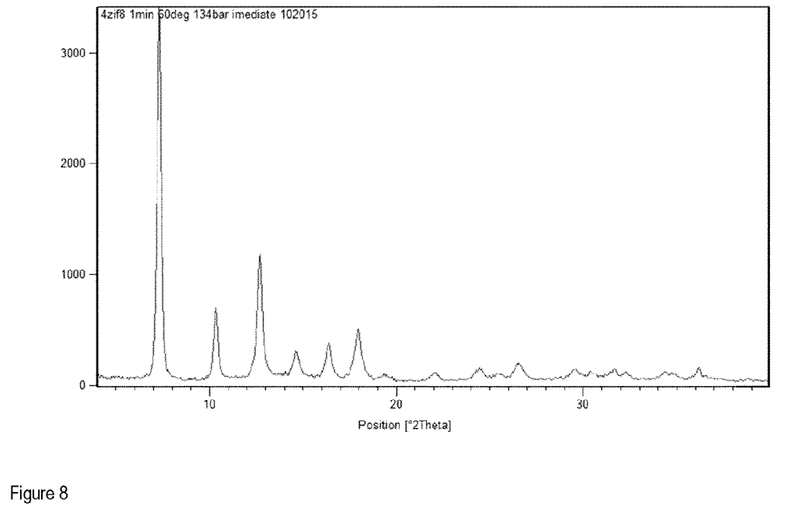
FIG. 8 shows the PXRD pattern for the reaction of ZnO and HMeIm after 1 minute at 60° C. and 130 bar in supercritical $CO_2$. The pattern corresponds to pure ZIF-8, in the presence of a small amount of ZnO reactant.
Figure 9:
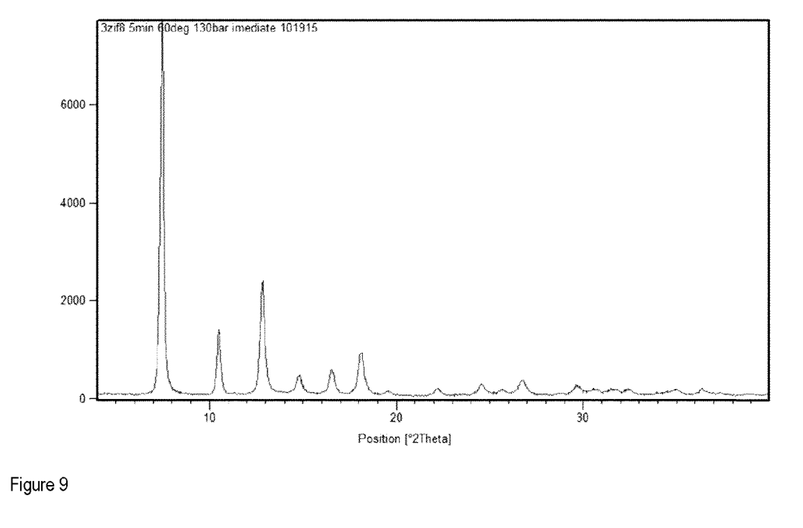
FIG. 9 shows the PXRD pattern for the reaction of ZnO and HMeIm after 5 minutes at 60° C. and 130 bar in supercritical $CO_2$. The pattern corresponds to pure ZIF-8.

Example 2—Accelerating the Synthesis of ZIF-8 in Supercritical CO$_2$ scCO$_2$ (supercritical CO$_2$) was again used as the medium for the synthesis of ZIF-8 starting from a 1:2 stoichiometric mixture of ZnO and 2-methylimidazole. The PXRD analysis (FIG. 8) shows that after 1 minute at 60° and 130 bar, the reaction was almost complete, with only a small amount of the ZnO reactant remaining. After 5 minutes in these conditions, the reaction was complete, the PXRD pattern (FIG. 9) showing ZIF-8 signals, but no signals associated with ZnO reactant.

Figure 10:
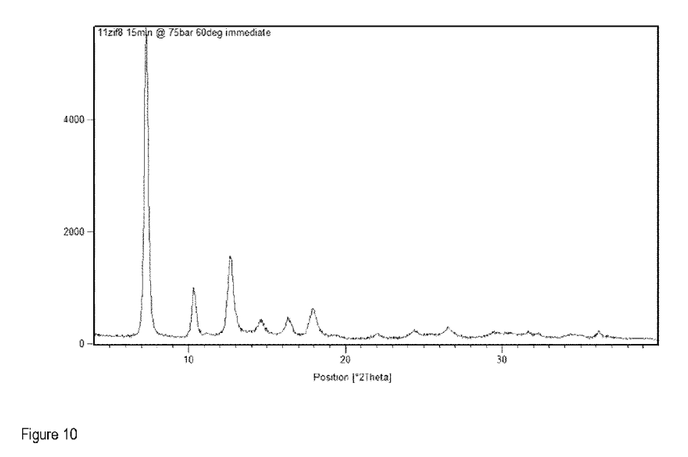
FIG. 10 shows the PXRD pattern for the reaction of ZnO and HMeIm after 15 minutes at 60° C. and 75 bar in supercritical $CO_2$. The pattern corresponds to pure ZIF-8, in the presence of a small amount of ZnO reactant.

In contrast, after 15 minutes at 60° and 75 bar, the PXRD analysis (FIG. 10) shows that the reaction is somewhat slower (but still quite fast compared to Example 1) since after 15 minutes, the reaction is almost complete, with only a small amount of the ZnO reactant remaining.

Example 3—Synthesis of ZIF-8 in Liquid CO$_2$

Figure 11:
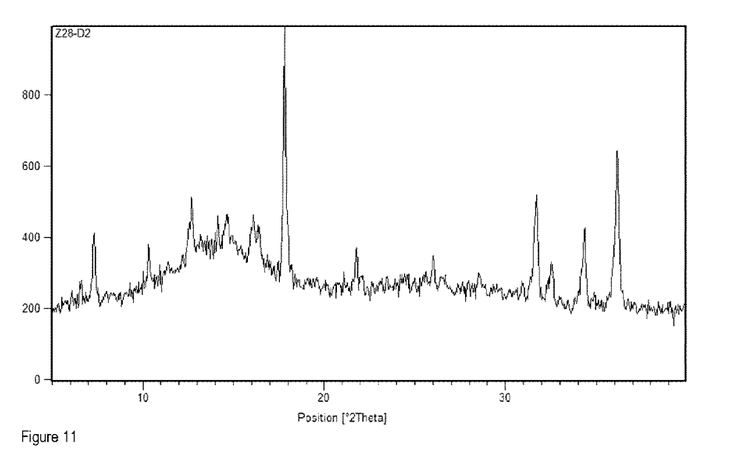
FIG. 11 shows the X-ray powder diffraction pattern of the product of Example 3.

The possibility to synthesize metal-organic frameworks in liquid CO$_2$ was explored by exposing a reaction mixture containing one equivalent of ZnO and two equivalents of HMeIm to liquid carbon dioxide at 25° C. and 70 bar. After 120 hours exposure, PXRD analysis revealed partial formation of ZIF-8 structure, recognized by characteristic reflections in the X-ray powder diffraction pattern (FIG. 11).

Example 4—Synthesis of a Copper(II) Isonicotinate MOF

Figure 12:
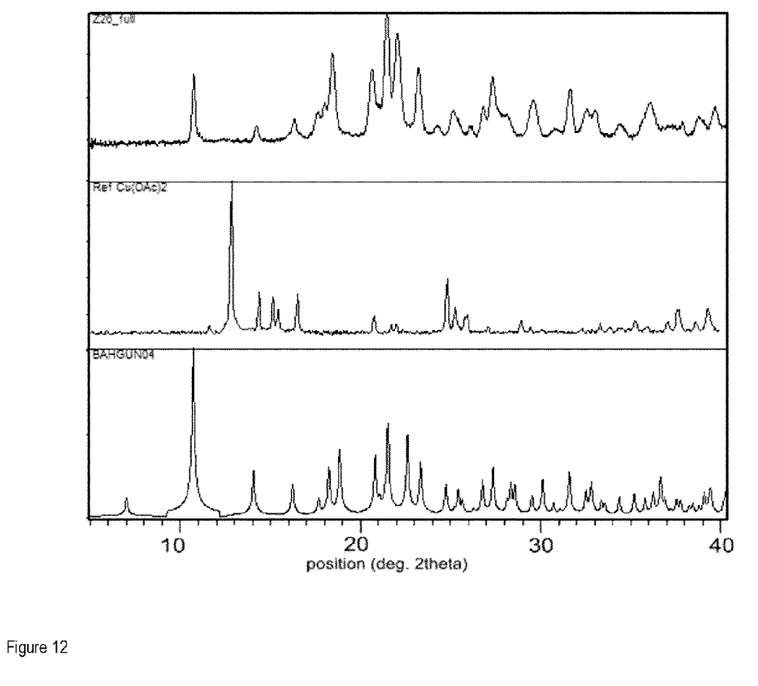

Synthesis of copper(II) isonicotinate was performed by exposing a mixture of 200 mg copper(II) acetate monohydrate and 123 mg isonicotinic acid to supercritical CO$_2$ at 100 bar and 100° C. for 6 hours. Analysis of the product by X-ray powder diffraction revealed the formation of the expected copper(II) isonicotinate framework (see FIG. 12 which compares the X-ray powder diffraction pattern of this product (top) with that of the copper(II) acetate monohydrate reactant (middle) and the pattern simulated for one of the reported crystal structures of the copper(II) isonicotinate framework (bottom), where the pattern simulated for the structure under the CSD code BAHGUN04 is shown).

Example 5—Synthesis of a Copper(II) Trimesate MOF

A copper(II) carboxylate MOF, known as HKUST-1 (one of the few currently available commercially made MOFs), has also been synthesised in supercritical carbon with or without using methanol as an additive.

Figure 13:
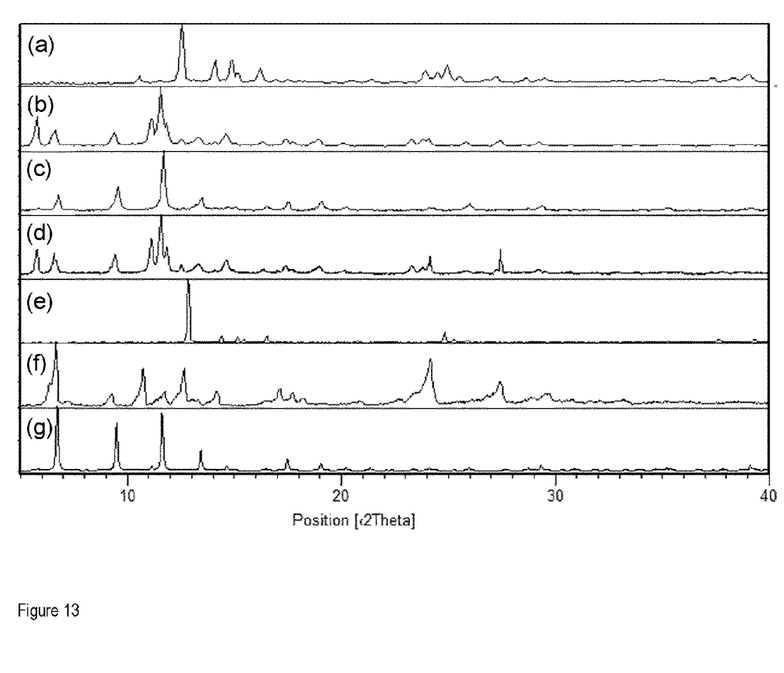
FIG. 13 shows the PXRD patterns for synthesis of the MOF material HKUST-1: (a) reaction mixture of copper(II) acetate monohydrate and trimesic acid before treatment in supercritical carbon dioxide; (b) the reaction mixture after 5 hours at 130 bar and 97° C.; (c) the reaction mixture after 2.5 hours at 130 bar and 97° C., after washing with methanol; (d) the reaction mixture after 5 hours at 130 bar and 100° C. in a fluid medium mixture of supercritical carbon dioxide and methanol; (e) copper(II) acetate monohydrate reactant; (f) trimesic acid reactant and (g) simulated for HKUST-1 (CCDC code FIQCEN).

Synthesis of copper(II) carboxylate was performed by exposing a mixture of copper(II) acetate monohydrate and trimesic acid to supercritical CO$_2$ at various pressures and temperature for various lengths of time. The powder X-ray diffractograms of the reaction mixtures involved are shown in FIG. 13 with those of the individual reagents and that simulated for the expected product. These PXRD patterns clearly show the formation of the HKUST-1 framework in all conditions, either as the only or the major product.

The scope of the claims should not be limited by the preferred embodiments set forth in the examples, but should be given the broadest interpretation consistent with the description as a whole.

REFERENCES

The present description refers to a number of documents, the content of which is herein incorporated by reference in their entirety. These documents include, but are not limited to, the following:

Park et al. in the Proc. Natl. Acad. Sci. USA 2006 103 (27) 10186-10191,
U.S. Pat. No. 8,466,284 (corresponding to International patent publication no WO 2077/023295),
Pichon et al., *CrystEngComm*, 2006, 8, 211-214,
Nelson et al. *J. Am. Chem. Soc.* 2009, 131, 458-460,
Farha et al. *J. Am. Chem. Soc.* 2012, 134, 15016-15021,
US patent application no. 2014/179514,
Beldon et al. *Angew. Chem. Int. Ed.* 2010, 49, 9640-9643,
Mottillo et al. *Green. Chem.* 2013, 15, 2121-2131,
Ibarra et al. *Green Chem.* 2012, 14, 117122,
Bayliss et al. *Green Chem.* 2014, 16, 3796-3802,
Banerjee et al. *J. Am. Chem. Soc.* 2009, 131, 3875-3877,
Zhang et al. *Chem. Rev.* 2012, 112, 1001-1033,
Batten et al. *CrystEngComm* 2012, 14, 3001-3004, and
Czaja et al. *Chem. Soc. Rev.* 2009, 38, 1284-1293.

The invention claimed is:

1. A method for the manufacture of a metal-organic compound, the method comprising the steps of:
   (a) providing at least one metal precursor,
   (b) providing at least one bridging organic ligand, and
   (c) exposing together the metal precursor and the ligand to liquid $CO_2$ or supercritical $CO_2$ as a reaction medium, thereby producing said metal-organic compound.

2. The method of claim 1, wherein during step (c), the metal precursor and the ligand are stirred with the liquid $CO_2$ or supercritical $CO_2$.

3. The method of claim 1, wherein during step (c), the metal precursor and the ligand are together exposed to supercritical $CO_2$.

4. The method of claim 1, wherein during step (c), the metal precursor and the ligand are together exposed to liquid $CO_2$.

5. The method of claim 1, wherein step c) is carried out at a temperature ranging between about 0° C. and about 100° C.

6. The method of claim 1, wherein step c) is carried out at a pressure ranging between about 80 bar and about 140 bar.

7. The method of claim 1, further comprising the step of (d) isolating the produced metal-organic compound from the liquid $CO_2$ or supercritical $CO_2$ by evaporating the liquid $CO_2$ or supercritical $CO_2$.

8. The method of claim 1, further comprising the step of (e) isolating the metal-organic compound from unreacted metal precursor and/or unreacted bridging organic ligand.

9. The method of claim 1, wherein the metal precursor contains a metal that is:
   from groups 1 to 12 of the Periodic Table, or
   Ga, Ge, In, Sn, Sb, Tl, Pb, or Bi, or
   a lanthanide.

10. The method of claim 1, wherein the metal precursor contains a metal in ionic form.

11. The method of claim 1, wherein the metal precursor contains a metal in the form of an oxide or a salt.

12. The method of claim 1, wherein the metal-organic compound is a metal-organic framework.

13. The method of claim 1, wherein the metal-organic compound is a zeolitic imidazolate framework.

14. The method of claim 13, wherein the metal precursor contains Zn.

15. The method of claim 13, wherein the ligand is a substituted or unsubstituted imidazole.

16. The method of claim 13, wherein the metal-organic compound is ZIF-8.

17. The method of claim 1, wherein the metal-organic compound is a carboxylate-based metal-organic framework.

18. The method of claim 17, wherein the metal precursor contains Cu(II).

19. The method of claim 17, wherein the ligand is a carboxylic acid or diacid.

20. The method of claim 17, wherein the metal-organic compound is copper(II) isonicotinate metal-organic framework or copper(II) trimesate metal-organic framework.

* * * * *